United States Patent [19]
Leonard et al.

[11] Patent Number: 5,882,849
[45] Date of Patent: *Mar. 16, 1999

[54] METHOD OF CONTROL OF HAEMATOCOCCUS SPP, GROWTH PROCESS

[75] Inventors: Alexander B. P. Leonard, Kailua-Kona; Mark E. Huntley, Honolulu, both of Hi.; Pearn P. Niiler, La Jolla, Calif.; Donald Redalje, Pass Christian, Mich.

[73] Assignee: Aquasearch, Inc., Kailua-Kona, Hi.

[ * ] Notice: This patent issued on a continued prosecution application filed under 37 CFR 1.53(d), and is subject to the twenty year patent term provisions of 35 U.S.C. 154(a)(2).

The term of this patent shall not extend beyond the expiration date of Pat. No. 5,541,056.

[21] Appl. No.: 673,063

[22] Filed: Jul. 1, 1996

Related U.S. Application Data

[63] Continuation-in-part of Ser. No. 279,740, Jul. 22, 1994, Pat. No. 5,541,056, which is a continuation-in-part of Ser. No. 23,172, Feb. 25, 1993, abandoned, which is a continuation of Ser. No. 729,707, Jul. 15, 1991, abandoned, which is a division of Ser. No. 663,669, Mar. 1, 1991, abandoned, which is a continuation-in-part of Ser. No. 419,522, Oct. 10, 1989, abandoned.

[51] Int. Cl.$^6$ .................................................. C12Q 3/00
[52] U.S. Cl. .................................... 435/3; 435/67; 435/166; 435/257.1; 47/1.4
[58] Field of Search .................................. 435/3, 41, 132, 435/166, 257.1, 257.3, 67, 257.6, 259, 292.1, 946; 47/1.4

[56] References Cited

U.S. PATENT DOCUMENTS 4,871,551  10/1989  Spenser ........................... 426/2
5,541,056  7/1996  Huntley et al. .................. 435/292.1

FOREIGN PATENT DOCUMENTS 2620131  3/1989  France .
2301587  11/1996  United Kingdom .
91-05849  5/1991  WIPO ............................. 435/292.1

OTHER PUBLICATIONS

"Enhancement and Determination of Astaxanthin Accumulation in Green Alga *Haematococcus pluvialis*," Sammy Boussiba, et al., *Methods in Enzymology*, vol. 213, 1992.

"Autotrophic growth and carotenoid production of Haematococcus pluvialis in a 30 liter air lift photobioreactor," Mark Harker, et al., *Chemical Abstracts*, vol. 125, No. 17, Abstract No. 219715, Oct. 21, 1996, Columbus, Ohio, USA.

*Primary Examiner*—William H. Beisner
*Attorney, Agent, or Firm*—Brown, Martin, Haller & McClain, LLP

[57] ABSTRACT

A control method for operating aqueous Haematococcus spp., such as *H. pluvialis*, microorganism growth processes is disclosed which can maintain viable growth conditions of this microorganism which have heretofore not been easily reproduced in commercially valuable quantities. The primary control parameters are the degree of turbulence in the aqueous growth medium and the scale of the apparatus relative to the scale of the turbulent eddies in vessels which are partially filled with the aqueous medium directly affect conditions which are required for optimum growth: light exposure, nutrient supply, sedimentation rate, bulk temperature, gas exchange rate and cell integrity. These control elements can be cast in terms of the Reynolds number ($N_{re}$), pH, temperature, amount of impinging light, and $NO_2$ concentration, depending upon the operative chlorophyll growth stages of Haematococcus spp. and its photoadaptive stages of producing astaxanthin.

13 Claims, 1 Drawing Sheet

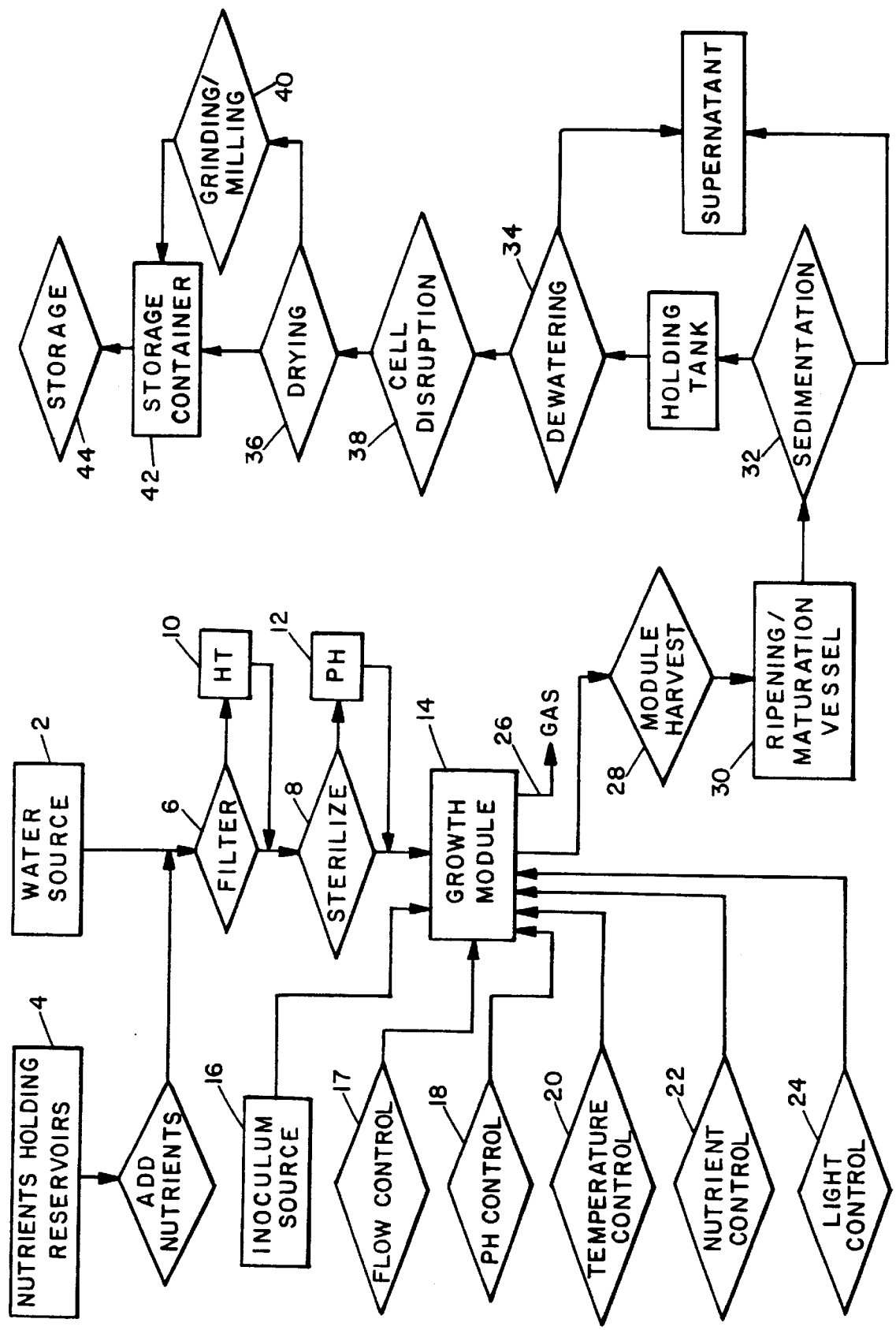

METHOD OF CONTROL OF HAEMATOCOCCUS SPP, GROWTH PROCESS

CROSS-REFERENCES TO OTHER APPLICATIONS

This application is a continuation-in-part of application Ser. No. 08/279,740, filed Jul. 22, 1994, now U.S. Pat No. 5,541,056; which in turn is a continuation-in-part of application Ser. No. 08/023,172, filed Feb. 25, 1993, now abandoned; which in turn is a continuation of application Ser. No. 07/729,707, filed Jul. 15, 1991, and now abandoned; which in turn is a division of application Ser. No. 07/663,669, filed Mar. 1, 1991, and now abandoned; which in turn is a continuation-in-part of application Ser. No. 07/419,522, filed Oct. 10, 1989, and now abandoned.

BACKGROUND OF THE INVENTION

1. Field of the Invention

The invention herein relates to the extraction of natural products from microorganisms, especially algae. More particularly it relates to control of large size aqueous photosynthetic bioreactor systems to obtain such products from the microbial genus Haematococcus, which has heretofore only been cultured in laboratory environments in small containers.

2. Description of the Prior Art

In view of environmental constraints, economics, and various other factors, astaxanthin, which is currently produced by chemical synthesis from petroleum- or coal-derived raw materials is coming into disfavor or is facing restrictions or outright bans from the marketplace. For instance, aniline-based sources of astaxanthin dyes are or will soon be phased out by government regulation in Europe, and similar restrictions or bans are likely to arise soon in other areas of the world, including the United States. Consequently there is a major research and development effort going on worldwide to find natural sources for astaxanthin.

It has been known that astaxanthin can be obtained from certain species of microorganisms, in particular those of the unicellular alga genus Haematococcus. Upon exposure to light, this alga genus produces astaxanthin by photosynthesis. If Haematococcus species, such as *H. pluvialis*, could be cultivated on a mass production basis, a valuable and economic natural source for this dye would be available.

The obvious utility of mass production of photosynthetic microorganisms resides in the process of photosynthesis itself. Given the appropriate supply of light, water, carbon dioxide ($CO_2$), and control of temperature, pH and the aqueous environment motions (e.g., turbulence), photosynthetic microorganisms can utilize sources of essential nutrients such as nitrogen (N) and phosphorous (P) to convert solar energy into chemical energy. Thus, the process of growing or culturing photosynthetic microorganisms involves the introduction of nutritionally complete medium to a contained volume of culture, maintenance of optimal growth conditions in that volume, and subsequent harvest or removal of the microbial cells from the spent medium. All culture programs must devise methods to accomplish each of these phases of the production process efficiently.

Of these requirements the most difficult to achieve is usually the step of maintaining optimum growth which equates to economically feasible production. Haematococcus species from which astaxanthin is derived are very sensitive, by an order of magnitude, to small changes in growth environment. It is common, for instance, for a researcher to develop a protocol for maintaining *H. pluvialis* in the laboratory in a small volume in a laboratory container, only to have the system fail dramatically in large size volume required for economic field production, where control of system parameters is much more difficult and more variables can be encountered.

For example, one photosynthetic growth mechanism, known as the "flashing light effect," i.e., the ability of some photosynthetic cells to effectively use energy from an intermittent light source [see, e.g. Emerson, et al., *J. Gen Physiol.*, 15(4):391–420 (1932)], has not been effectively utilized in a mass culture system, because it depends on the turbulent flow regime in the growth media that exposes cells intermittently to a light source. Too much or too little exposure results in decreased production of microorganisms. A method or apparatus has been developed by Applicants which maximizes the flashing light effect by use of controlled turbulent flow regime such that this effect could be utilized in a mass culture system, thus enhancing the efficiency and productivity of that system for Haematococcus spp.

It has been known that one must avoid excessive shear in the fluid on the scale of the microorganism, in order to prevent destruction of the microbial mass. For instance, Thomas et al., *J. App. Phycology*, 2:71–77 (1990) reported that in small gap rotating cylinders at Reynolds Numbers above 116 (and up to 3500) cell growth rate became negative, i.e., that the microbial mass was dying, not growing. Thus, the dimensions or mechanical configuration of the apparatus must also be controlled in order to alleviate the deleterious effects of turbulence on cell integrity.

The concept of culturing microorganisms in open or closed systems and harvesting a product from the microorganisms is not new. There are numerous systems used throughout the world in which algae or phytoplankton are grown and harvested, either for direct usage (as for animal food) or for indirect usage (as sources of chemicals such as carotenes). However, almost all such systems operate on only a very few species of microorganisms; i.e., those which have been found to be tolerant to the widest range of growth conditions and which produce relatively simple products. This in turn has limited the industry to production of a very small number of products compared with what has been extracted in laboratory scale, experimental cultures. Efforts that have been made to culture Haematococcus for production of astaxanthin have been failures because laboratory cultures have not been made to survive or grow economically in large scale volumes. Furthermore, Haematococcus spp. which will tolerate the fairly crudely controlled processes of the past (either open or closed systems) have not been capable of yielding astaxanthin, either directly or indirectly, in economical quantities. Haematococcus has not proved amenable to culture in the current systems, since such systems cannot be controlled in a sufficiently precise manner to maintain adequate health and growth of Haematococcus which may have been grown on a small scale in a laboratory. Laboratory scale apparatuses generally do not contain turbulent flows, while commercial production scale systems do. Heretofore, the necessity of control of turbulence has not been recognized as a crucial factor in mass culture apparatus, as the Applicants have found to be necessary for the health of Haematococcus microorganisms.

Numerous operating conditions or factors are critical in commercially viable production of astaxanthin from condition-sensitive Haematococcus spp. Consequently, a system in which precise control of these operating conditions is accomplished will permit not only large scale culturing of Haematococcus spp., which cannot now be grown by existing commercial technology, but also the mass production of natural astaxanthin which is not currently available on an economic basis in the marketplace.

SUMMARY OF THE INVENTION

The specification of the environmental conditions for Haematococcus spp., as exemplified by *H. pluvialis*, has now been addressed. The present invention is a control method for operating an aqueous microorganism growth process as defined generally in the previous U.S. Pat. No. 5,541,056, so as to maintain optimum and thus commercially viable growth conditions for Haematococcus spp. which has heretofore not been reproduced in commercially valuable quantities. We have discovered that such processes can be precisely and continuously controlled and can sustain the commercially viable growth of Haematococcus spp., and particularly *H. pluvialis* and its synthesis of astaxanthin than has been possible with prior art processes and control methods. The primary control parameters in this invention are: i) the degree of turbulence, ii) the size/configuration of vessels which are either closed to the atmosphere, or in which communication with the atmosphere is restricted or controlled, and which are partially filled with the aqueous medium, iii) light exposure, iv) nutrient supply, v) bulk temperature, and vi) cell longevity within the growth media. Thus, we have been able to successfully produce large scale quantities of Haematococcus spp. on a sustained basis by utilizing aqueous medium turbulence and apparatus environment control as essential control parameters for optimum growth. Failure to control turbulence levels or environment in the apparatus leads to failure of system operations, less than optimum growth and failure of commercial viability (as demonstrated in Thomas, supra).

Therefore, the invention is the specification for the control of an aqueous Haematococcus and astaxanthin synthesis growth process which comprises distributing a photosynthetic Haematococcus biomass in an aqueous medium within a reaction chamber, the reaction chamber being transparent to visible light, and the aqueous medium containing the suspension of Haematococcus biomass occupying less than the total volume of the chamber; maintaining the biomass within the reaction chamber for a 1–5 day period of time during which microorganisms comprising the biomass reproduce, increase in number, and retain their astaxanthin synthesis potential; providing nutrients to and removing evolved gases from the biomass during the period of time to support the reproduction; flowing quantities of the aqueous medium at a rate of 2–100 cm/sec through the reaction chamber throughout the time period; subjecting the reaction chamber to an amount of visible light in the range 50–1000 $\mu Em^{-2}sec^{-1}$ for at least a portion of the period of time with the visible light passing into the reaction chamber and being used by the microorganisms to enable photosynthesis; maintaining a turbulent flow regime with Reynolds Number in the range of 2000 to 50,000 throughout the aqueous medium within the reaction chamber for the period of time; maintaining a temperature in the chamber in the range of 16°–27° C. over the the time; maintaining a pH in the range of 7.2 to 7.8 in the chamber over the period of time; maintaining an $NO_3^-$ control in the range of 4 to 12 mmoles/L in the chamber over the period of time; at the end of the period of time harvesting the grown biomass from the reaction chamber and passing it to a ripening/maturation vessel; maintaining a turbulent flow regime with a Reynolds Number in the range of 20,000 to 70,000 within the ripening/maturation vessel; and maintaining a range of ambient light of 1500 to 2600 $\mu Em^{-2}sec^{-1}$ in the vessel; such that in the turbulent flow regimes effective reaction conditions are maintained for the reproduction of the Haematococcus microorganisms until the time period has been sufficient to produce a desired increase in Haematococcus and subsequently in production of astaxanthin by the Haematococcus.

In the present process of control, turbulence is characterized by two parameters: its time scale (t) and the space scale, L, of its predominant eddies (the scale in which viscous processes become important). The time scale of the turbulent eddies controls the time Haematococcus spp. spends in the light intensive zone of the apparatus, and thus its control of the intensity of incident light is just as important. The combination of L and t, as (L/t), defines the velocity scale of turbulence, q, and q controls the vertical rate of transport of Haematococcus spp. microorganisms. q must be larger than the settling velocity of *H. pluvialis* in order to keep it in suspension. Nutrient delivery to the cells is controlled by choosing optimum lengths ($L_K$) of apparatus so as to not overstress the cell walls of the algae and by choosing the ambient level of nutrients. Removal of oxygen, which is deleterious to microorganisms at high concentrations, is accomplished by allowing turbulence to access significant areas of free surface in the partially filled container. The control of bulk temperature is achieved by both turbulence levels as well as cooling of reactor walls. pH control is achieved by $CO_2$ control in the vessel.

These control elements related to turbulence can be cast, first, in terms of the Reynolds number ($N_{Re}$). Secondly, controlled dimensions of the apparatus ($L_K$) must be specified in relationship to the scales of turbulent eddies, expressed as $\lambda_K = L_K/L$. Alternately, the second criteria can be recognized as a specification of the dissipation rate of mechanical energy in the fluid, $\epsilon$, which for a given Reynold's number allows L to be quantified for delivery of nutrients to the cell. In the present process, control of turbulence is maintained in two different steps, each with its own range of Reynolds Numbers ($N_{Re}$), and level of fluid free surface is controlled so as to exert control over the degree of light intensity, nutrient delivery, sedimentation rate, gas exchange, temperature and length of residence time in the reactor to which Haematococcus spp. can be exposed to obtain the optimum yield of astaxanthin. The broadest ranges of Reynolds Numbers generally useful in this invention are, for the growth step, $N_{Re}$=2000 to 50,000, preferably 5000 to 40,000, more preferably 10,000 to 30,000, and for the astaxanthin production step, $N_{Re}$=20,000 to 70,000. For the level of fluid in the flowing-fluid reaction chamber relative to eddy scale, $\lambda_K$, is in the range of 0.1–1 reaction chamber volume unit, and preferably in the range of 0.1–0.8. For these turbulent conditions, the ambient light levels must be maintained at 50–1000 $\mu Em^{-2}sec^{-1}$, nutrient levels at 4–12 mmoles/L of $NO_3^-$, pH of 7.2–7.8 ($CO_2$ levels), temperature of 16° C.–27° C., and length of incubation time 1–5 days in controlled reactor chambers.

In a preferred embodiment of the invention, the particular species of Haematococcus is *H. pluvialis*.

BRIEF DESCRIPTION OF THE DRAWING

The FIGURE is a flow diagram illustrating an exemplary *H. pluvialis* production process utilizing the control method of the present invention. The control method is utilized in the design and operation of the growth module and ripening/maturation vessel segments of the process.

DETAILED DESCRIPTION AND PREFERRED EMBODIMENTS

For brevity herein, the invention will be described in terms of the exemplary species *H. pluvialis*. It will be understood, however, that the invention and the description and claims herein are applicable to the entire genus Haematococcus, although of course those skilled in the art will recognize that there will be minor variations in specific conditions and yield for different species within the genus.

There are currently two types of aqueous systems for the growth of microorganisms such as *H. pluvialis*. In first type, the operator produces and harvests common types of microorganisms for animal and human food consumption and for extraction of chemicals such as astaxanthin. These systems may be closed, but often are open, and use as their raw materials microorganisms which have relatively low sensitivity to reaction conditions. Simple exposure to sunlight, access to common nutrients which are coarsely dispersed in the aqueous medium, and minimal control of operating parameters such as temperature, mixing, gas exchange and the like characterize these systems. Process control often consists of little more than deciding when to stop and start the medium circulation devices and how often to inject nutrients into the medium. Such systems work quite well for production of only several species of microorganisms, and they are found throughout the world, particularly in hot and sunny climates.

However, such conventional systems have not been found capable of effectively producing *H. pluvialis*, which is much more sensitive to the conditions of their growth environment. No *H. pluvialis* culture in such typical fermentation devices have shown commercial success to date. The present system, by contrast, provides light and turbulence control not provided in standard fermentation devices. Production of *H. pluvialis* on an economic scale is highly desirable, since this microorganism produces astaxanthin. Unfortunately, sufficiently close and precise control of the growth environment parameters has heretofore only been possible in laboratory or equivalent small scale processes. When developers have attempted to scale up such processes, the results have usually been either an inability to duplicate the growth rates of the laboratory or short-term growth followed by mass death of the *H. pluvialis* population.

There are a number of operating conditions which we have found to be important parameters to produce significant, economic and sustainable growth of the "condition-sensitive" *H. pluvialis*. These include received light, residence time in "growth modules," type and amount of available nutrients, sedimentation rate of microorganisms, uniformity and absolute value of fluid temperature of the growth medium, ability of the medium to provide for adequate gas exchange, $CO_2$ delivery or acidity (pH), turbulence levels of the aqueous medium during various stages of the microorganism growth cycle, and the factors which control the successful production of astaxanthin in this cell. An important element in this process is the recognition that for commercially viable production of *H. pluvialis* and astaxanthin, these parameters must be controlled within limits that have been discovered by the inventors by experimentation and testing in commercial size production facilities. Different microalgae have different limits and this invention sets the control limits for *H. pluvialis* in commercial scale (>1000 L) reactors. This unique and combined system of control has not been present or recognized in the prior art's small scale laboratory systems, nor would it be expected from such systems.

A critical feature of the present invention for the commercially viable growth of *H. pluvialis* is that the precise combination of controls be exercised. Light exposure process is primarily controlled by control of the degree of turbulence in the aqueous medium and control of the scale of the apparatus to the scale of the turbulent eddies. This sets the time cells spend in a lighted environment. Aqueous media which contain a commercially viable diversity of *H. pluvialis* cells are relatively opaque due to cell density and the extinction length of light we have measured to a few centimeters. In this context, the level of turbulence must be maintained such that the time the microorganism spends near the light exposed surfaces of the apparatus is larger than it spends in the opaque media. This is accomplished in this invention by recycling the *H. pluvialis* cells near the free surface of the flowing media in the partially filled growth module, and the degree of turbulence controls the recycling. The level of ambient light must also be carefully controlled for *H. pluvialis* cells to reproduce rapidly. Control of the level of turbulence in the medium also directly affects gas exchange rates or pH. Levels of bulk temperature and availability of nutrients to the cells must be maintained. Oxygen must be removed continually; this latter is accomplished via recycling of the turbulent eddies coming in contact with the free surface of the partially filled growth module. Important also is the sedimentation rate during the growth process. If cells are allowed to settle on the bottom or the walls of the growth module, light penetration is inhibited and the immobile cells become detritus which harbor hostile bacteria and produce unwanted effects. Thus, as noted, in properly designed apparatus we have been able to successfully produce large scale quantities of *H. pluvialis* on a sustained basis by utilizing aqueous medium turbulence, controlled light levels, temperature, nitrate concentration, and culture residence time as the operative control parameters. The specification and control of the unique combination of these parameters is necessary for commercially viable production of *H. pluvialis* and the ability of *H. pluvialis* to synthesize astaxanthin.

Reynolds Number Control:

It is known that there are two principal regimes in flowing fluids, a laminar flow regime which is characterized by streamlines which remain distinct from one another over the given length of the fluid flow, and a turbulent flow regime which is characterized by an overall zone of flow instability in which eddies are generated which produce a disruption of the streamlines' flow pattern. In systems where there is an overall flow translation, e.g., a bulk fluid flow from one end of a conduit to the other, the turbulent flow regime is superimposed on the primary bulk translational flow, so that the result is a highly mixed flow stream with the mixed fluid moving along the prescribed flow path.

The transition from laminar flow to turbulent flow in a fluid body and the degree of turbulence in that body depends on the rate of movement of the fluid, the parameters of the flow conduit, and the viscosity of the fluid. Turbulence (and laminar flow) are most commonly defined numerically by a dimensionless quantity called the Reynolds Number ($N_{Re}$) which is of the form ($L_K V/\sigma$), where $L_K$ is (as defined above) a characteristic linear dimension of the conduit, V=average flow speed of the bulk fluid flow, and $\sigma$=fluid kinematic viscosity. The "critical Reynolds Number" [$N_{Re}$ (crit)] is the $N_{Re}$ value of the transition from laminar flow to turbulent flow in the fluid of interest. For circular conduits $N_{re}$(crit)=2000–4000, depending upon the wall roughness of the conduit; i.e., transition from laminar flow beings at $N_{Re}$<2000 and a turbulent flow regime is well established once $N_{Re}$=4000. There is no specific upper limit to values of $N_{Re}$, with published tables commonly showing highly turbulent regimes with $N_{Re}$ up to $10^8$, although for flow in conduits of common materials fluids tend to reach a maximum turbulence regime at $N_{Re}$ values of about $10^6$ and thereafter higher values of $N_{Re}$ generally do not signify substantially more turbulence in the fluid. Derivation and explanation of Reynolds Number are found in many fluid dynamics handbooks and textbooks; see, e.g., Chilton (ed.), *Chemical Engineers' Handbook*, pp. 5-4 and 5-20 to 5-26 (5th edn.: 1973); Condon et al. (eds.), *Handbook of Physics*, Part 3, Ch. 2 (1958); Eshbach (ed.), *Handbook of Engineering Fundamentals*, Sect. 6, Parts 2, 6 and 9 (2nd edn.: 1952); Weast (ed.), *Handbook of Chemistry and Physics*, p. F-330 (65th ed.: 1984); and O'Brien et al., *Applied Fluid Mechanics*, pp. 105–110 (1st edn.: 1937).

Note that when the turbulent flow regime is mentioned herein, and especially when it is discussed as being essentially throughout the aqueous medium in the reaction vessel, it will be understood that some small degree of laminar flow regime will necessarily also be present, normally in the boundary layer immediately adjacent to the vessel walls. It is known that in any flowing fluid conduit, a viscous Prandtl boundary layer will form at the surface of the vessel walls, with the layer including a laminar flow region at the wall transistioning to a turbulent flow region in the body of the fluid. The degree of turbulence in the body of the fluid will affect the overall thickness of the laminar boundary layer next to container walls but does not eliminate it. Therefore those skilled in the art will recognize that for the purposes of this invention, the reference to the turbulence control will be with respect to the bulk of the fluid, notwithstanding the presence of a minimal amount of laminar flow regime present in the system. See, for instance, McCabe et al, *Unit Operations of Chemical Engineering*, pp. 45–48 (1956).

Since a turbulent regime is not established at the same $N_{Re}$ in all systems, or in a single dynamic system and the width of the transition $N_{Re}$ range from laminar to fully turbulent flow is a function of at least two parameters of the system, the liquid flow rate and the wall surface characteristics of the closed flow conduit, control of turbulence in a closed system requires that the operator carefully monitor both of these parameters. Since the surface characteristics, such as smoothness of the conduit walls, change only slowly over time and are not within the control of the operator of the system on a real time basis, the operator utilizes flow rate to control turbulence. As noted above, some transitional turbulence occurs at $N_{Re}<2000$, and full turbulence is present at $N_{Re}$ values in the range of 4000 to $10^6$ depending on the degree of smoothness of the conduit.

In the present process the operator will control Reynolds Number according to the specific step involved, to obtain turbulence which is correlated with the degree of light intensity and cooling (or heating) medium which controls the temperature to which *H. pluvialis* can be exposed to obtain the optimum yield in that step. In the growth step, Reynolds Number will change as the culture grows, both because of the change in effective viscosity of the medium due to increase in cell density (which may reduce turbulence) as well as the change of opacity of the medium to light penetration, which requires more frequent visits near the free surface of the fluid in the container. Typically, after inoculation of a culture of *H. pluvialis* into the reactor, $N_{Re} \approx 2000$. As the culture of *H. pluvialis* matures, $N_{Re}$ increases to about 30,000 or higher. The range of $N_{Re}=2000$ to 50,000 is the broadest for practical purposes in this process for growing *H. pluvialis*, although it is preferred to be in the range of $N_{Re}=5000$ to 40,000, more preferably (after start-up) $N_{Re}=10,000$ to 30,000. It is possible to have $N_{re}$ as high as $10^6$ or higher, but also as mentioned there is little or no significant increase in the level of turbulence above $10^6$, so no significant change in the operation of the present process is obtained. In fact such higher values may be detrimental in that additional pumping power for the greater water flow is needed, greater shearing of the microorganism mass may occur without any countervailing improvement in microbial growth and long chain structures of the microorganism will be broken. On the other hand, $N_{Re}$ must not be too low, since if there is no substantial turbulent regime, the microbial cells well settle out of the medium, the system will become too dense, and there will be little light penetration. In the subsequent astaxanthin production step, Reynolds Numbers are usually in the range of 20,000 to 70,000. The prior art has not heretofore recognized or described such correlation between the degree of turbulence and the maintenance of *H. pluvialis* growth rate within the optimum range defined for *H. pluvialis*.

Exemplary Apparatus Configuration and Control of Optimum Values of Environmental Parameters for Growth of *H. pluvialis*:

The basic principles and processes involved in the application of the control parameters and the assumed mechanisms described above will be better understood when discussed in the context of an exemplary *H. pluvialis* growth system. Such a typical system is illustrated schematically in the FIGURE. The system may be considered as having three principal functions: water pretreatment, microbe production, and harvesting. Such a system may be capable of maximum conservation of water resources by recycling all water not subject to evaporation. It will be understood that the control parameters of this invention are applied in the bioreactor growth module 14, i.e., the *H. pluvialis* production component. (There may be a plurality of growth modules 14 operating in parallel, but for brevity herein the description will be given in terms of a single growth module 14.)

In the water pretreatment stage, fresh water is obtained from a water source 2 and mixed with nutrients from a nutrient holding reservoir 4. The mixture is preferably passed through a filter 6 and sterilizer 8, and then may be pumped into a large holding reservoir 10. Filtration may be accomplished by a combination of a variety of conventional techniques ending in microfiltration. Preferably the cover of the holding reservoir will be made from a dark plastic material, e.g., black polyethylene, to prevent contamination of the prefiltered water and promote heating without exposing the prefiltered water to sunlight, which can encourage unwanted premature growth of photosynthetic microorganisms in the holding reservoir.

It may be desirable to preheat the water/nutrient mixture, which can be accomplished at 12 by, e.g., passive solar heating in a covered holding reservoir (which may be the same as reservoir 10). The preheating process may be necessary in the case of relatively cool source water, such as non-geothermal ground water which may be at a lower temperature than is required for optimal growth of *H. pluvialis* (between about 16°–27° C. [61°–81° F.). Thus, preheating permits the temperature of the culture to be adjusted appropriately prior to introduction into the circulating growth system. When the water from the source is already at an appropriate culture temperature, the preheating step can be eliminated. Further, while solar heat is preferred for economic and environmental reasons, other sources of heat such as a conventional heater could be used to provide the necessary temperature adjustment.

The sterilization step 8 may be necessary in the case of source water expected to contain living microorganisms or potential predators, which might threaten the viability of the desired microorganisms being grown in the culture system. The preferred method of sterilization is by treatment of the medium with ultraviolet light, gamma radiation, ozone, or any other noninvasive sterilization agent, or it may also be accomplished by other conventional means. In many cases, the prior filtration step can be expected to eliminate living particles. If analysis of the source water or effectiveness of the filtration indicates no substantial contamination of the water with unwanted microorganisms or potential predators, the sterilization step is not required.

The *H. pluvialis* feedstock is provided to an appropriate reaction vessel or "bioreactor," here defined as a growth module 14, for the first operating step, that of biomass growth and chlorophyll production. Makeup water (which may be conditioned with nutrients and other desired additives) and a microorganism inoculum 16 are introduced directly into a growth module. There is an initial period of growth of inoculum in the module 14, which will generally last for only a few days. This is the period of lowest Reynolds Number regime. Thereafter, as the microorganism grows and the biomass increases, there is continued addition of fresh makeup water and nutrients, either manually or automatically, while the turbulent regime increases in intensity. Continued expansion of the system to full operating capacity is a simple matter of replication.

Nutrients are normally added to the water as it enters the growth module 14 as indicated at 16. In the production state, water is distributed from the holding reservoir 10 through the sterilization processor 8 to individual growth modules 14. If the holding reservoir is maintained at a higher elevation than the growth modules, distribution from the holding reservoir can be accomplished under the force of gravity. Otherwise, a pump is required to feed the water into the growth module 14. Recirculating liquid flow within the growth module system will be controlled at 17 by restriction of the inlet line (in the case of a gravity head system) or by pump control in a pumped system. Optimum $NO_3^-$ levels for *H. pluvialis* growth are in the range of 4–12 mmoles/L, with the lower values being necessary for the final growth stage.

The growth module 14 will be greater in volume than the volume of the aqueous medium, i.e., the growth module is not completely filled with the aqueous medium. This is necessary so that the benefits of effective turbulence can be achieved. If the module is full, there is a wall effect which causes cells to accumulate at the wall and become trapped there, causing light saturation of those cells and, by blocking light, causing light starvation of the cells in the interior of the aqueous medium. If the module is kept only partially filled, there is a free medium surface present which permits effective turbulent motion of the bulk medium and prevent the accumulation of stagnant cell masses at the conduit surface. Further, substantial oxygen gas is evolved during cell growth. If the growth module is full of the aqueous medium, removal of the evolved oxygen gas is hindered and the cells in the system can suffer oxygen poisoning. Finally, keeping the module less than full of the aqueous medium means that the system can operate at essentially ambient pressure instead of overpressure, and that ordinary transparent flexible tubing can be used as the conduit in the growth module, rather than requiring expensive pressure resistant rigid tubing. The filled volume can be any convenient amount, and will generally be in the range of about 30%–90%. If the volume is too close to completely full, the wall effect and gas removal problems will predominate, while if the volume is too low, the system will not be utilized efficiently. Those skilled in the art will be readily able to determine an appropriate fill volume for any particular apparatus.

Typically the growth modules 14 are tubular and made at least partly of polyethylene, although any rigid or flexible material not harmful to plant tissue can be used providing it is substantially insoluble and impermeable to water, transparent to visible light, but impervious to near-visible ultraviolet light. While low density polyethylene is most preferred for this purpose (particularly if it is of minimum thickness so as to reduce both light attenuation and cost), other possible materials include polypropylene, polyacrylate, polyamide, polycarbonate, water insoluble cellulose ester and polyester films, or (less preferred) glass.

The growth module 14 will commonly be provided with a means 26 for collecting dissolved gases, such as oxygen, which are produced during photosynthesis by the microorganisms being grown therein. Also, addition of $CO_2$ at 18 is needed for regulating pH and for providing carbon molecules for photosynthesis. *H. pluvialis* requires pH in ranges of 7.2–7.8 for cell survival. Temperature control 20 is exercised by a joint control of turbulence (or $N_{Re}$) and by regulation of the wall temperature of the growth module. The temperature range for optimum production of *H. pluvialis* during lighter, turbulent conditions is 16°–27° C., depending upon whether the cells are in dividing (day) or resting (night) conditions. Optimum light levels are maintained at 24 by the recirculation of the turbulent eddies and by providing appropriate illumination through the growth process. *H. pluvialis* cells are photoadaptive and sensitive to light. In an initial period of 1–5 days in the growth module 14, when chlorophyll is produced, the light impinging on the free surface of the bioreactor will be in the range of 50–1000 $\mu Em^{-2}sec^{-1}$, with a maximum of about 150–175 $\mu Em^{-2}sec^{-1}$ light intensity when the culture is first introduced into the modules. This light level is raised to a maximum of 100–800 $\mu Em^{-2}sec^{-1}$, preferably 130–500 $\mu Em^{-2}sec^{-1}$, during full operating conditions of growth. Light level control is achieved through partial screening of sunlight when the growth module is operated out of doors. It will be understood that ambient light out of doors varies through the course of a day. However, although the light levels will change during the day, it is necessary that for at least a significant portion of the day the light levels must be in the specified ranges for effective control to be possible. The same will be true of the light levels for the astaxanthin production step described below.

Nutrient control at 22 may consist of injection of additional nutrients at various time intervals during the growth process within the growth module 14. The specific time intervals will be selected based on the level of nutrients in the growth module at any given time. The growth module, which is described in greater detail hereinafter, may be characterized as a closed, controlled, continuous growth environment for growth of *H. pluvialis*.

In the second operating stage of the process, that of astaxanthin production (synthesis), cells are harvested from the reaction module 14 to ripening/maturing vessel 30 (as indicated at 28), where the synthesis of astaxanthin in the *H. pluvialis* cell occurs during the process of photoinhibition. This latter process requires the administration of light levels in the range of about 1500 to 2600 $\mu Em^{-2}sec^{-1}$ for periods of several hours to several days. The *H. pluvialis* culture that is drawn from the growth module 14 is diluted in vessel 30 by a factor of 1–5 and no new nutrients are added. The ripening/maturation vessel 30 may be open or closed, but must continue to have a free surface for effective exchange of gases. Harvesting begins from vessel 30 when the astaxanthin content of the cells has reached a desired level. The turbulence levels at this time are at $N_{Re}$=20,000 to 70,000, to keep the astaxanthin-containing cells in suspension. Harvesting of *H. pluvialis* is normally accomplished by a separation process, preferably a multi-stage process, with concentration of *H. pluvialis* biomass increasing at each step until a final wet or dry product is obtained. In the example shown in the FIGURE the biomass is harvested from ripening/maturation vessel 30 when the rate of continued growth and astaxanthin production drop below a predetermined value. The cells and water are separated in several steps; first a rough separation by sedimentation 32, followed by dewatering 34 and drying 36.

For astaxanthin to be commercially utilized it must be released from the *H. pluvialis* cells. After dewatering and drying, the cells must be broken at 38 by a cell-rupturing method such as by milling, for instance with a bead mill, or ultrasonification.

The dried astaxanthin may be ground or milled to a desired uniform size distribution at 40 and then packed and stored for shipment at 42 and 44. The degree of drying in unit 36 will be controlled for final moisture content. Those products with higher residual water content are frequently referred to as "wet" astaxanthin, as compared to the "dry" astaxanthin products with lower residual water content. Use applications for astaxanthin-containing *H. pluvialis* product exist for both wet as well as dry product.

It will be recognized that the control parameters applied to growth of *H. pluvialis* in module 14 will vary over the course of each growth cycle, since as microbial growth develops the various requirements of light availability to increasing numbers of cells, nutrient requirements and delivery, total gas generation, temperature, etc. will vary. Thus the method of the present invention will be recognized to be a continuous control method, where the turbulence control level and other parameters at any time is a function of the progress of the microbial growth cycle.

During operation of the system, the physical, chemical and biological characteristics of the growth medium for *H. pluvialis* are continuously monitored, usually at several monitor stations across the system. Properties commonly monitored include pH, temperature, optical density (biomass), flow velocity, incident light, $NO_3$, and the health of the cells. Acceptable values of each will vary over the specified ranges dependent upon the time within the production cycle, and those skilled in the art will be able readily to determine the optimum values within these ranges for these properties at the specific stage in the process of *H. pluvialis* growth and astaxanthin synthesis. These will change also with the residence time of the microorganisms in the growth module. As guidance, we have found that when, e.g., *Haematococcus pluvialis* is grown in a system of the type illustrated in the FIGURE with 24 cm diameter closed conduits, suitable ranges of parameters are:

| | |
|---|---|
| $N_{Re}$ in growth module | 2000–50,000 |
| pH | 7.2–7.8 |
| $CO_2$ content | 100 $g/m^3$ to solubility limit |
| temperature | 16°–27° C. |
| $NO_3^-$ | 4–12 mmoles/L |
| flow velocity | 2–100 cm/sec |
| length of time in modules for optimum astaxanthin production | 1–5 days |
| Ambient light levels for *H. pluvialis* growth in the growth module | 50–1000 $\mu Em^{-2}sec^{-1}$ |
| Ambient light levels for astaxanthin synthesis in ripening/maturation vessel | 1500–2600 $\mu Em^{-2}sec^{-1}$ |
| $N_{Re}$ in ripening/maturation vessel | 20,000–70,000 |

It will be evident that there are numerous embodiments of this invention which, while not expressly described above, are clearly within the scope and spirit of the invention. The above description is therefore to be considered exemplary only, and the actual scope of the invention is to be determined solely from the appended claims.

We claim:

1. A method for the control of aqueous Haematococcus and astaxanthin synthesis growth process which comprises:

distributing a photosynthetic Haematococcus biomass in an aqueous medium within a reaction chamber, said reaction chamber being transparent to visible light, and said aqueous medium containing said suspension of Haematococcus biomass occupying less than the total volume of said chamber;

maintaining said biomass within said reaction chamber for a 1–5 day period of time during which microorganisms comprising said biomass reproduce, increase in number, and retain their astaxanthin synthesis potential;

providing nutrients to and removing evolved gases from said biomass during said period of time to support said reproduction;

flowing quantities of said aqueous medium at a rate of 2–100 cm/sec through said reaction chamber throughout said time period;

subjecting said reaction chamber to an amount of visible light in the range 50–1000 $\mu Em^{-2}sec^{-1}$ for at least a portion of said period of time with said visible light passing into said reaction chamber and being used by said microorganisms to enable photosynthesis;

maintaining a turbulent flow regime with Reynolds Number in the range of 2000 to 50,000 throughout said aqueous medium within said reaction chamber for said period of time;

maintaining a temperature in said chamber in the range of 16°–27° C. over the said time;

maintaining a pH in the range of 7.2 to 7.8 in said chamber over said period of time;

maintaining an $NO_3^-$ control in the range of 4 to 12 mmoles/L in said chamber over said period of time;

at the end of said period of time harvesting the grown biomass from said reaction chamber and passing it to a ripening/maturation vessel;

maintaining a turbulent flow regime with a Reynolds Number in the range of 20,000 to 70,000 within said ripening/maturation vessel; and maintaining a range of ambient light of 1500 to 2600 $\mu Em^{-2}sec^{-1}$ in said vessel;

such that in the turbulent flow regimes effective reaction conditions are maintained for said reproduction of said Haematococcus microorganisms until said time period has been sufficient to produce a desired increase in Haematococcus and subsequently in production of astaxanthin by said Haematococcus.

2. A method as in claim 1 wherein each said turbulent flow regime causes movement of said Haematococcus such that exposure of individual microorganisms to said visible light is intermittent.

3. A method as in claim 2 wherein said intermittent exposure of visible light to Haematococcus creates a flashing light effect on photosynthesis produced in said microorganisms.

4. A method as in claim 3 wherein said Haematococcus microorganisms are exposed to said visible light for a cumulative time of approximately ten times longer than the cumulative time of non-exposure.

5. A method as in claim 1 wherein said aqueous medium containing said biomass occupies approximately 30%–90% of the total volume of said reaction chamber.

6. A method as in claim 1 wherein said Haematococcus microorganism comprises Haematococcus spp.

7. A method as in claim 6 wherein said Haematococcus spp. comprises *H. pluvialis*.

8. A method as in claim 1 wherein said Reynolds Number in said turbulent flow regime in said reaction chamber in the range of 5000–40,000.

9. A method as in claim 8 wherein said Reynolds Number in said turbulent flow regime in said reaction chamber in in the range of 10,000–30,000.

10. A method as in claim 1 wherein said amount of visible light to which said reaction chamber is exposed in in the range of 100–800 $\mu Em^{-2}sec^{-1}$.

11. A method as in claim 10 wherein said amount of visible light to which said reaction chamber is exposed in in the range of 130–500 $\mu Em^{-2}sec^{-1}$.

12. A method as in claim 1 further comprising passing said Haematococcus cells from said ripening/maturation vessel to a cell rupturing step wherein said cells are ruptured to free astaxanthin.

13. A method as in claim 12 wherein said rupturing comprises subjecting said cells to milling or ultrasonification.

* * * * *